United States Patent [19]

Hilal et al.

[11] 4,084,209
[45] Apr. 11, 1978

[54] ROTATING SUPERCONDUCTOR MAGNET FOR PRODUCING ROTATING LOBED MAGNETIC FIELD LINES

[75] Inventors: Sadek K. Hilal, Englewood Cliffs, N.J.; William B. Sampson, Bellport, N.Y.; Edward F. Leonard, Leonia, N.J.

[73] Assignee: The United States of America as represented by the United States Department of Energy, Washington, D.C.

[21] Appl. No.: 688,873

[22] Filed: May 21, 1976

[51] Int. Cl.² .......................... H01L 39/14; H01F 7/22
[52] U.S. Cl. .................................... 361/141; 128/1.4; 323/44 F; 335/216
[58] Field of Search ....................... 361/141; 335/216; 323/44 F; 128/1.3, 1.4, 1.5

[56] References Cited

U.S. PATENT DOCUMENTS

| | | | |
|---|---|---|---|
| 3,098,189 | 7/1963 | Buchhold | 323/44 F |
| 3,278,808 | 10/1966 | Bonfeld | 361/141 |
| 3,402,347 | 9/1968 | Nelson | 361/141 |

Primary Examiner—Gerald Goldberg
Attorney, Agent, or Firm—Dean E. Carlson; Leonard Belkin

[57] ABSTRACT

This invention provides a rotating superconductor magnet for producing a rotating lobed magnetic field, comprising a cryostat; a superconducting magnet in the cryostat having a collar for producing a lobed magnetic field having oppositely directed adjacent field lines; rotatable support means for selectively rotating the superconductor magnet; and means for energizing the superconductor magnet.

9 Claims, 4 Drawing Figures

ROTATING SUPERCONDUCTOR MAGNET FOR PRODUCING ROTATING LOBED MAGNETIC FIELD LINES

BACKGROUND OF THE INVENTION

This invention was made in the course of, or under a contract with the United States Energy Research and Development Administration, or its predecessor, the United States Atomic Energy Commission.

In the field of medicine it is desirable to guide intravascular devices, such as catheters, within the human body. Heretofore, however, these devices were limited in their applications or did not operate properly for routine work, since they were pushed slowly by hand, such that friction was a problem, particularly after the device went around a bend in a vessel, or they were otherwise inefficient and troublesome, or involved other difficult and time consuming problems.

SUMMARY OF THE INVENTION

This invention overcomes the problems known heretofore by providing a selectively rotatable and selectively positionable superconducting magnet having corresponding persistent and selectively rotatable field lines having four lobes that intercept a ferro-magnetic intravascular device within a vessel within the human body to pull the device while making the device flutter so as to reduce friction between the device and the inside of the vessel wall by rapidly, sequentially, periodically and selectively bringing different portions of the device into contact with the vessel wall.

OBJECTS OF THE INVENTION

It is an object of this invention to overcome the problems known heretofore by providing a rotating, persistent field, dc, superconducting magnet for variably pulling ferro-magnetic intravascular devices while fluttering the same within the human body.

The above and further novel features and objects of this invention will appear more fully from the following detailed description of one embodiment when the same is read in connection with the accompanying drawing, and the novel features will be particularly pointed out in the appended claims.

BRIEF DESCRIPTION OF THE DRAWINGS

In the drawing where like elements are referenced alike:

FIG. 1a is a partial cross-section of a patient on a table that is movable in three directions to bring the desired part the patient near the rotating superconducting magnet of FIG. 1. FIG. 1b is a partial cross-section of the apparatus of FIG. 1 along the X—X plane, normal to the Z—Z axis.

DETAILED DESCRIPTION OF ONE EMBODIMENT

This invention is useful for variably pulling ferromagnetic intravascular devices within the human body in the treatment of vascular malformations, such as large abnormal channels that shunt blood from arteries to veins, by using silicon-based polymer carried by a ferro-magnetic catheter. Ferro-magnetic catheters can also be used, in accordance with this invention, to deliver silicon resin or similar material to block the blood supply to tumor cells, to guide catheters that are used to administer drugs and radioactive substances to cancerous areas in a very precise fashion, thus permitting a high local concentration of the anti-cancer agent, and to guide intracranial catheters, which are found to be more sensitive than skin electrodes in recording the intracranial electrical activity of the brain. In fact, this invention is useful in any application where it is advantageous to pull a catheterer and to cause flutter in a ferro-magnetic device, e.g., to reduce friction by allowing only portions of the ferro-magnetic device to touch the vessel wall at any one time.

Figure 1:
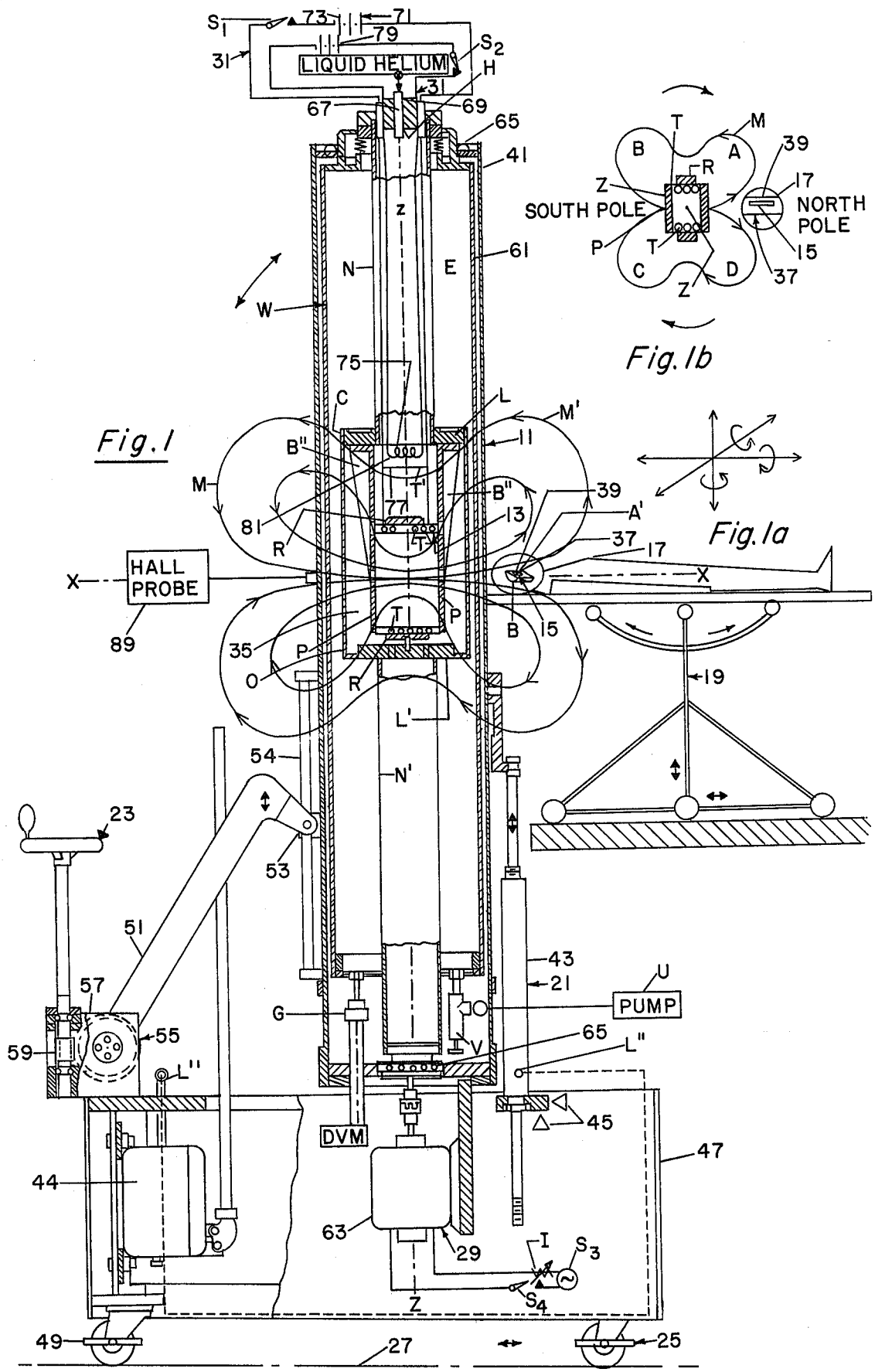
FIG. 1 is a partial cross-section of one embodiment of the rotating magnet of this invention.
Figure 2:
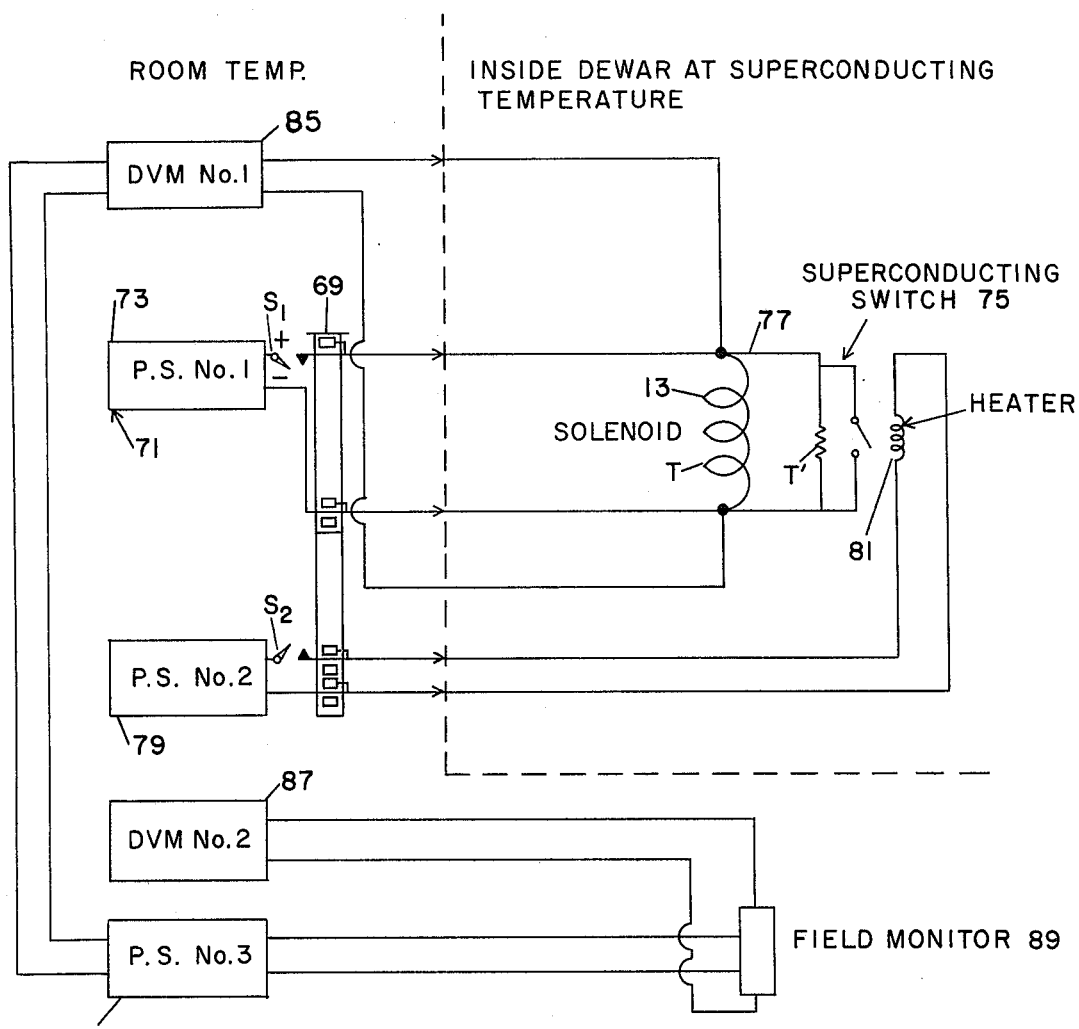
FIG. 2 is a partial schematic view of one embodiment of the electrical system for the rotating superconducting magnet of FIG. 2.

Referring now to the figures, FIG. 1 is a partial cross-section of one embodiment 11 of the rotating, persistent field, dc, superconducting, solenoid magnet 13 of this invention for producing a rotating, persistent, dc, four-lobed magnetic field M for causing a variable pulling force and a flutter in the ferro-magnetic intravascular devices 15 within the human body 17. As shown in FIG. 1a, which is a partial cross-section at a reduced scale from FIG. 1 the patient on table 19 is movable horizontally and vertically, and selectively rotatable in horizontal and vertical planes at right angles relative to each other and relative to the rotating superconductor magnet 13 of FIG. 1. FIG. 1a is shown at reduced scale to illustrate the proximity of a typical position to the magnet of FIG. 1. FIG. 1 shows the systems 21, 23, and 25 (the latter on floor 27) for changing the position of the rotating field M so that in combination with the table 19, the magnet can be positioned in substantially any direction and/ or any angle relative to the patient and/or the catheterer device 15. FIG. 1b illustrates the rotating lobes A, B, C and D of the magnetic field fo FIG. 1. FIG. 2 illustrates the electrical system for producing the persistent, dc, rotating magnetic field of FIG's. 1 and 1b.

The magnet 13, comprises a simple solenoid coil that is symmetrically wound around an X—X axis normal to the selectively positionable axis of rotation Z—Z as shown in FIG. 1. By placing an iron balancing collar R centered on the X—X axis around the magnet solenoid, the magnetic field lines are constrained into a toroidal, symmetric, doughnut shape with each equipotential field line in a plane oppositely passing through the axis of rotation Z. The iron collar R encircles and supports partially potted, partially porous turns T of magnet 13 around axis X—X between non-magnetic plates L and L' normal to plates O and P having braces B'' to produce the lobes A, B, C and D by locally short-circuiting the flux lines so that from the view of FIG. 1b they are kidney-shaped to form the desired four clover leaf-shaped lobes.

The magnet 13 is rotated by means 29, having means 31 for producing the persistent current in the magnet 13 to produce persistent rotating field line M' forming lobes A, B, C and D, as shown in FIG. 1b, that rotate around the axis of rotation Z, alternately-sequentially to intercept the ferro-magnetic intravascular device 15 within the human body 17 shown in FIG. 1a, to pull the device toward the magnet while causing the device to flutter. When a persistent current is desired, the rotation of the magnet is stopped and the magnet is plugged into a power source. Later, the power source is unplugged and the magnet is again rotated as described in more detail hereinafter. By rotatating the superconductor, around the selectively positioned axis of rotation Z with a persistent current in the magnet, the magnet produces endless field lines that are tied to the inside of the magnet annulus 35 as these field lines and lobes rotate around the axis of rotation and intercept the ferro-magnetic intravascular device 15 within a longitudinally extending vessel 37 so that the one end of the device, as it comes closest to the magnet 13, periodically alternately takes on a first polarity that pulls the device towards the magnet with a first net force, and, as the magnet rotates, different field lines are intercepted alternately periodically to change the polarity of that end of the device to cause the device to be pulled toward the magnet 13 again and again with a net pulling force. This causes the device to be pulled toward the magnet and to flutter so as to reduce its friction with the vessel wall 39 by rapidly, sequentially, periodically and selectively bringing different portions A' and B' of the device 15 into contact with various portions of the vessel wall 39.

The magnet 13 is contained in an outer selectively positionable and selectively stationary fiberglass and epoxy container 41 that is mounted on hydraulic cylinders 43 having pumps 44 connected through lines L" therewith for forming the height means 21, which in turn is mounted on support pivots 45 tied to the rollable carriage 47, the latter which is mounted on rotatable casters 49 forming the rotation means 25 that freely rotate in the carriage and roll on floor 27. A lever arm 51 forms the vertical angle means 23 and has a slide 53 that moves up and down on the outside of the rod 54 on the outer selectively positionable and selectively stationary container 41. The lever is connected to a gear train 55 having a first gear 57 that rotates a second gear 59 connected to the lever to cause the lever to slide up and down on the outer container 41, thus to tilt it at continuously variable angles to the vertical.

The inner non-magnetic cylinder 61 forms a cryostat W, which is rotated by a continuously variable frequency motor 63 mounted on the outer container 41 so that the motor rotates the inner cylinder on bearings 65 mounted between the inner and outer cylinders 41 and 61.

There is a cryostat vacuum between the rotatable cylinder 61 and the helium filled cylinders in space E. To this end the vacuum is pulled by pump U through valve V. This vacuum is monitored by remote sensing means through plug G, and the inner stainless steel containers N and N' are filled through hole H with liquid helium that seeps down by gravity through the spaces between the porous turns T of the magnet 13 or holes in plates L, L' and P. The containers N and N' fill with liquid helium to cool the superconducting magnet 13 to a temperature below its critical superconducting temperature. To this end, the containers N and N' are filled by selectively removing cap 67.

A persistent current is produced in the magnet by plugging a suitable power source into the plug 69 in the top of the inner container 61, so that the electrical system 71 produces the desired persistent current in the magnet 13. One suitable superconductor is NbT, but alternately one can use the $Nb_3Sn$ superconductor described in U.S. Pat. No. 3,638,154, which is incorporated by reference herein.

The electrical system 71, which is shown in FIG. 2, comprises a power source 73 that causes current to flow through the magnet 13 and a superconducting switch 75, which forms an endless superconducting circuit 77 when closed. This switch is selectively closed by removing current flow from power source 79 to coil 81, which causes the superconducting circuit to be cooled to a temperature below its critical superconducting temperature, thereupon closing the circuit 77. A third power source 83 drives suitable digital volt meters 85 and 87 connected respectively to the magnet and a field monitor 89.

In operation, the desired magnetic field is monitored by the Hall probe 89 shown in FIG. 1, while the patient is positioned vertically in height, rotated at continuously variable frequencies around the vertical and located at the desired slant by manipulating the table 19 on floor 27 to position the ferromagnetic device within the body 17 at the desired location and in the desired direction. Then the magnet 13 is positioned as desired by adjusting the height means 21, the vertical angle means 23 and the rotation means 25. To this end, the vertical height is controlled by pumping hydraulic fluid from pump 44 to cylinders 43, one of which is shown for ease of explanation. The vertical angle of the magnet 13 and its axis of rotation Z is manipulated by selectively rotating the gears 57 and 59 to raise or lower the slide 53 along the side of the outer cylinder 41. Rotating the carriage 47 on casters 49 rotates and positions the magnet on floor 27 around a desired position of the axis of rotation Z. Then the motor 63 is continuously variably energized continuously variably to rotate the cryostatic containers N and N' in outer container 61.

When a persistent current is desired in the magnet 13, the rotation is stopped, and the first power source is plugged into the plug 69 while the switch 75 is closed to provide an endless superconducting circuit due to the liquid helium in the inner container 61.

Then the power source 79 is connected through plug 69 to heater element 81 to heat portion T' of endless superconducting circuit 77. This causes portion T' to become normally resistant, thus opening the superconducting circuit 77. Then, the power source 73 energizes the magnet 13 by closing switch $S_1$, and plugging the source 73 into plug 69. When the magnet is fully energized, switch $S_2$ opens to disconnect power source 79 from heater 81. This causes portion T' to become superconducting again, whereupon the ends of endless circuit 77 are again connected, and plug 69 is disconnected to remove sources 73 and 79. Also motor 63 is energized from a suitable source $S_3$, by closing switch $S_4$ to rotate the inner containers, 61 and N and N' and its magnet 13 inside the outer container 41. The speed of the motor is continuously variable by conventional means, such as variac I.

As the magnet 13 rotates with cylinders N, N' and 61, the four lobes of the field M alternately periodically intercept the respective ends of the ferro-magnetic device 15, as shown in FIG. 1b, thus sequentially to modulate their polarization and to pull them toward the magnet with a net fluttering force, while causing them to flutter back and forth in the vessel containing them. As can be seen from FIG. 1b this causes the device 15 to be intercepted sequentially periodically alternately with field lines whose directions alternate oppositely, as shown by the arrows in FIG. 1b, as they pass through the human and device 15 shown therein, and this interception can be while the patient and apparatus are relatively stationary and/or while one or both are being positioned, e.g., by hand on table 15 and/or with means 21, 23 and 25, in any arbitrary direction.

This invention has the advantage of providing a self-contained, selectively positioned, rotating superconductor magnet having a persistent current for producing a four lobed magnetic field having field lines tied to the inside of the magnet annulus sequentially periodically alternately to intercept a ferro-magnetic intravascular device to modulate the polarity of its ends. By selectively positioning the magnet, its four lobes and the ferro-magnetic device, and by selectively rotating the magnet, the magnet causes the device to be pulled toward the magnet and to flutter within a vessel from side to side so as to reduce its internal friction with the vessel by rapidly, sequentially, periodically and selectively intercepting the ends of the device with field lines whose directions alternate oppositely adjacently to produce the desired modulation.

What is claimed is:

1. A rotating superconductor magnet, comprising:
   a. a cryostat;
   b. a superconducting magnet in the cryostat having an iron collar for producing a four lobed magnetic field having oppositely directed adjacent field lines;
   c. rotatable support means for selectively rotating the superconductor magnet in a first direction in a first plane at continuously variable frequencies in the cryostat; and
   d. means for energizing the superconductor magnet with a persistent current to produce a persistent magnetic field to produce the four lobed magnetic field lines around the magnet that extend beyond its immediate vicinity, so that the magnet is selectively rotated at continuously variable frequencies to produce a rotating magnetic field having rotating field lines and lobes having opposite field line directions extending beyond the immediate vicinity of the magnet.

2. The apparatus of claim 1 having means for selectively vertically biasing the cryostat, magnet and rotatable support means.

3. The apparatus of claim 2 having means for selectively rotating the cryostat, magnet and rotatable support means at continuously variable frequencies.

4. The apparatus of claim 3 having means for selectively rotating the cryostat, magnet and rotatable support means in a second direction in a horizontal plane at continuously variable frequencies, when the rotatable support means is rotating the superconductor magnet in a first direction in the first plane.

5. The apparatus of claim 1 in which the means for energizing the magnet with a persistent current, comprises:
   a. a solenoid forming the magnet;
   b. switching means that is connected in series to the opposite ends of the solenoid for selectively forming an endless superconducting circuit;
   c. power source means for energizing the solenoid through the switching means;
   d. means for opening and closing the switching means to open and close the endless superconducting circuit; and
   e. means for selectively connecting and mechanically disconnecting the power source means from the solenoid when the endless superconducting circuit is closed so that the solenoid contains a persistent current and is disconnected from the power source means for the continuous rotation fo the solenoid.

6. The apparatus of claim 1 in which the cryostat, comprises:
   a. stationary container means;
   b. rotatable container means inside the stationary container means containing the superconductor magnet;
   c. bearings between the stationary container means and the rotatable container means;
   d. drive means connected to the rotatable container means and supported on the stationary container means for rotating the rotatable container means in the bearings; and
   e. means for selectively filling the rotatable container means with cryogenic cooling fluid to maintain the superconductor magnet below its critical superconducting temperature while it is being rotated in a stationary container means by said drive means.

7. The apparatus of claim 6 having:
   a. means for rotating the stationary container means in a horizontal plane;
   b. means for rotating the stationary container means in a vertical plane; and
   c. means for selectively biasing the stationary container means vertically correspondingly selectively to vertically bias and to rotate the rotatable container means in horizontal and vertical planes while the rotatable container means is being rotated in the stationary container means by said drive means.

8. The apparatus of claim 7 in which the vertical drive means for selectively vertically biasing the stationary container means has hydraulic actuating means.

9. The apparatus of claim 8 in which the means for selectively rotating the stationary container means in a vertical plane has:
   a. rotatable first and second gear means;
   b. lever means connected to the second gear means;
   c. slide means connected to the lever means and the stationary container means for selectively moving the lever means up and down the slide means when the first gear means is rotated; and
   d. pivot means for supporting the vertical drive means while permitting the same vertically selectively to bias the stationary container means, and while permitting the first and second gear means to cause the stationary container means to be selectively rotated in a vertical plane by selectively sliding the lever means up and down the slide means.

* * * * *